United States Patent
Lu et al.

(10) Patent No.: US 9,845,274 B2
(45) Date of Patent: Dec. 19, 2017

(54) CHROMIUM-FREE CATALYST FOR GAS-PHASE FLUORINATION AND APPLICATION THEREOF

(71) Applicant: XI'AN MODERN CHEMISTRY RESEARCH INSTITUTE, Shaanxi (CN)

(72) Inventors: Jian Lu, Shaanxi (CN); Bo Wang, Shaanxi (CN); Yue Qin, Shaanxi (CN); Wei Mao, Shaanxi (CN); Liangang Kou, Shaanxi (CN); Zhenhua Zhang, Shaanxi (CN); Fei He, Shaanxi (CN); Wei Zhang, Shaanxi (CN); Hui Ma, Shaanxi (CN); Yangbo Ma, Shaanxi (CN); Zhijun Hao, Shaanxi (CN); Chunying Li, Shaanxi (CN); Yongmei Du, Shaanxi (CN); Fengxian Li, Shaanxi (CN); Sheng Han, Shaanxi (CN)

(73) Assignee: XI'AN MODERN CHEMISTRY RESEARCH INSTITUTE, Shaanxi (CN)

( * ) Notice: Subject to any disclaimer, the term of this patent is extended or adjusted under 35 U.S.C. 154(b) by 0 days.

(21) Appl. No.: 15/103,803

(22) PCT Filed: Aug. 5, 2014

(86) PCT No.: PCT/CN2014/083679
§ 371 (c)(1),
(2) Date: Jun. 10, 2016

(87) PCT Pub. No.: WO2015/085781
PCT Pub. Date: Jun. 18, 2015

(65) Prior Publication Data
US 2016/0311736 A1   Oct. 27, 2016

(30) Foreign Application Priority Data
Dec. 12, 2013 (CN) .......................... 2013 1 0680436

(51) Int. Cl.
| | |
|---|---|
| *B01J 37/26* | (2006.01) |
| *B01J 23/83* | (2006.01) |
| *B01J 27/128* | (2006.01) |
| *C07C 17/20* | (2006.01) |
| *C07C 17/25* | (2006.01) |
| *C07C 21/18* | (2006.01) |

(52) U.S. Cl.
CPC .............. *C07C 17/206* (2013.01); *B01J 23/83* (2013.01); *B01J 27/128* (2013.01); *B01J 37/26* (2013.01); *C07C 17/25* (2013.01)

(58) Field of Classification Search
CPC . B01J 27/128; B01J 37/26; B01J 23/83; B01J 23/135; C07C 17/25; C07C 17/206; C07C 21/18
See application file for complete search history.

(56) References Cited

U.S. PATENT DOCUMENTS

| | | |
|---|---|---|
| 3,231,519 A | 1/1966 | Clark |
| 3,322,692 A | 5/1967 | Clark |
| 5,773,671 A | 6/1998 | Tung |

FOREIGN PATENT DOCUMENTS

| | | |
|---|---|---|
| CN | 1078172 A | 11/1993 |
| CN | 1098332 A | 2/1995 |
| CN | 1111606 A | 11/1995 |
| CN | 1408476 A | 4/2003 |
| CN | 1680029 A | 10/2005 |
| CN | 101028991 A | 9/2007 |
| CN | 101913986 A | 12/2010 |
| CN | 101961658 A | 2/2011 |
| CN | 102527414 A | 7/2012 |
| EP | 0 514 932 A2 | 11/1992 |

OTHER PUBLICATIONS

International Search Report, dated Nov. 18, 2014, for International Application No. PCT/CN2014/083679, 6 pages.

Primary Examiner — Jafar Parsa
(74) Attorney, Agent, or Firm — Seed IP Law Group LLP

(57) ABSTRACT

Disclosed in the present invention is a chromium-free catalyst for gas-phase fluorination and an application thereof. The precursor of the related chromium-free catalyst for gas-phase fluorination consists of a compound containing iron element, a compound containing rare earth metal element and a compound containing element A, wherein element A is one selected from Ca, Al, Mg and Ti, the precursor is subjected to calcination and fluorination treatment to obtain the chromium-free catalyst for gas-phase fluorination. The precursor of the catalyst is calcined at 400-500° C. and fluorinated with hydrogen fluoride at 350-450° C. to obtain the chromium-free fluorinated catalyst. The catalyst has characteristics of being chromium-free and environment-friendly, good catalytic activity and long life etc. The catalyst can be used for preparing hydrofluoroolefins or hydrochlorofluoroolefins from halohydrocarbons.

6 Claims, No Drawings

CHROMIUM-FREE CATALYST FOR GAS-PHASE FLUORINATION AND APPLICATION THEREOF

TECHNICAL FIELD

The present invention relates to a chromium-free catalyst for gas-phase fluorination and use thereof. Particularly, the present invention relates to a chromium-free fluorinated catalyst used for preparation of hydrofluoroolefins (HFOs) or hydrochlorofluor oolefins (HCFOs) through gas-phase fluorination of halohydrocarbons.

BACKGROUND

In fluorine chemical industry, gas phase fluorination of halohydrocarbons is often used for preparation of hydrofluoroolefins and hydrochlorofluoroolefins, which has the following advantages: simple devices, easiness for continuous large-scale production, safety and the like. Fluorinated catalysts play a critical role in gas-phase fluorination reaction of halohydrocarbons. Presently, the catalysts for gas-phase fluorination used industrially are chromium-containing fluorinated catalysts.

Chinese Patent No. CN94106793.9 disclosed that a fluoride precursor was prepared by the precipitation of a mixture of $Cr(NO_3)_3$ and $In(NO_3)_3$ with ammonia water, and then the precursor was subjected to calcination and fluorination with HF to obtain a fluorinated catalyst composed of indium, chromium, oxygen and fluorine.

U.S. Pat. No. 5,773,671 disclosed that a blend of $Al_2O_3$ and $Cr_2O_3$ was impregnated in $CoCl_2$ solution, and then subjected to drying, calcination, and fluorination to obtain a fluorinated catalyst.

EP0514932A3 disclosed that $Cr_2O_3$ with a specific surface area of more than 170 $m^2\ g^{-1}$ was prepared by a precipitation method, and then subjected to fluorination to obtain a fluorinated catalyst. Moreover, it does not disclose the addition of other co-catalysts.

CN01141970.9 disclosed that an amorphous catalyst precursor with a specific surface area of more than 200 $m^2\ g^{-1}$ and a pore volume of more than 0.3 $m^2\ g^{-1}$ was prepared by reacting an aqueous solution of soluble salts of chromium and other components with a precipitant (an alkaline substance) at 20-100° C., and then subjected to calcination and activation to obtain a fluorinated catalyst of $CrM_{0.3}Mg_{0.1}O_{0.5}F_{2.0}$.

Catalysts for gas-phase fluorination used in practice are mostly chromium-containing catalysts. It has been demonstrated that chromium-containing compounds are toxic, and thus would damage human digestive tract and kidney. Moreover, high-valence chromium has a strong carcinogenic effect, and thereby production and use thereof would do harm to human and environment.

In order to solve the above-mentioned problems, the chromium-containing fluorinated catalyst needs to be replaced with a chromium-free fluorinated catalyst. For example, CN107817A and CN1111606A disclose a chromium-free catalyst, wherein zinc is loaded onto alumina, halogenated alumina or haloalumina, but the catalyst has a low catalytic activity. CN1680029A discloses a chromium-free catalyst, wherein an antimony halide ($SbF_nCl_{5-n}$) is loaded onto calcium fluoride, but the catalyst has a low catalytic activity. Moreover, the antimony halide is apt to run off during fluorination and the catalyst has a poor thermal stability.

In conclusion, the existing chromium-free catalysts have some drawbacks, such low activity, and easy running-off, and thus they have no practical value.

SUMMARY OF THE INVENTION

With respect to the defects and deficiencies in the prior art, one object of the present invention is to provide a gas phase fluorination catalyst which is chromium-free and has a long service life and a good catalytic activity.

In order to solve the above-mentioned technical problems, the present invention provides a chromium-free gas phase fluorination catalyst, the precursor of which consists of a compound containing iron element, a compound containing rare earth metal element and a compound containing element A, wherein the element A is one selected from Ca, Al, Mg and Ti, and the precursor is subjected to roasting and fluorination treating to obtain the chromium-free gas phase fluorination catalyst.

Preferably, the precursor of the catalyst comprises the iron element, the rare earth metal element and the element A with the following mass percentage composition: 5.0%-50.0% of the iron element, 0.5%-5.0% of the rare earth metal element, and 45.0-94.5% of the element A; and the sum of the mass percentage of the three elements is 100%.

Preferably, the precursor of the catalyst is roasted at 400-500° C. and then fluorinated with hydrogen fluoride gas at 350-450° C. to obtain the chromium-free gas phase fluorination catalyst.

Preferably, in the precursor of the catalyst, the compound containing iron element is an oxyhalide of iron, a metallic salt compound of iron, an oxide of iron, a hydroxide of iron, an organic salt containing the iron element or a complex containing the iron element; the compound containing rare earth metal element is a metallic salt compound of the rare earth metal element, an oxide of the rare earth metal element, a hydroxide of the rare earth metal element, an organic salt containing the rare earth metal element or a rare earth double salt containing the rare earth metal element; and the compound containing element A is an oxyhalide of the element A, a metallic salt compound of the element A, an oxide of the element A, a hydroxide of the element A, an organic salt containing the element A or a complex containing the element A.

Preferably, the iron element in the precursor of the catalyst is ferric iron in a crystal form of α, β, γ, or δ.

Preferably, the compound containing rare earth metal element is a single compound containing the rare earth metal element or a composition of two or more compounds containing the rare earth metal element, wherein the rare earth metal element is one selected from Sc, Y, Ce, La, Nd, Pr, Pm, Sm, Eu, Gd, Tb, Yb, Ho, Dy, Er, Tm, Yb and Lu.

With respect to the defects and deficiencies in the prior art, another object of the present invention is to provide use of said chromium-free gas phase fluorination catalyst for preparation of hydrofluoroolefins and hydrochlorofluoroolefins by using halohydrocarbons as raw material.

As compared with the prior art, the present invention has the following advantages:

(1) There are fewer industrial wastes such as waste gas, waste water and waste residues and a person skilled would not contact with toxic substances such as chromium during the production and application of the chromium-free gas phase fluorination catalyst according to the present invention, and thus the catalyst is environmentally friendly.

(2) In the present invention, $Fe^{3+}$ is preferably used as an active component of the catalyst. The key of the fluorine/ chlorine exchange reaction lies in the presence of $F^{-1}$ in unsteady state, $Fe^{3+}$ has a covalent radius similar to that of $Cr^{3+}$, and thus more $F^{-1}$ in unsteady state may be formed in the fluorination reaction, facilitating the occurrence of the fluorine/chlorine exchange reaction. $Fe^{3+}$ has 4 different crystal forms, i.e., α, β, γ, and δ. At the same time, a rare earth metal is used as co-catalyst. Rare earth metal compounds have relatively strong oxygen storage ability. In a rare earth doped composite catalyst, the rear earth metal compound has a center for adsorbing oxygen on the surface of the catalyst, which may suppress carbon deposition on the catalyst, thereby prolonging the life of the catalyst. For example, when HCFO-1233xf or HCFO-1233zd is synthesized by gas phase fluorination, the life of the catalyst is more than 1,000 hours.

(3) The chromium-free gas phase fluorination catalyst according to the present invention has a long service life and a good catalytic activity, and thus is suitable for preparation of various HFOs and HCFOs by gas phase fluorination. For example, HFO-1234ze was synthesized by gas phase fluorination of HCFO-1233zd; HCFO-1233xf was synthesized by gas phase fluorination of HCC-240ab; HCFO-1233xf was synthesized by gas phase fluorination of HCC-240db; HCFO-1233xf was synthesized by gas phase fluorination of HCC-1230xf; HCFO-1233xf was synthesized by gas phase fluorination of HCC-1230xa; HFO-1243zf was synthesized by gas phase fluorination of TCP; HCFC-244bb was synthesized by gas phase fluorination of HCFO-1233xf; HCFO-1233zd was synthesized by gas phase fluorination of HCC-240fa; HFO-1234ze was synthesized by dehydrochlorination of HCFC-244fa; HFO-1234ze was synthesized by dehydrofluorination of HFC-245fa; HFO-1234yf was synthesized by dehydrochlorination of HCFC-244bb; HFO-1234yf was synthesized by dehydrofluorination of HFC-245eb; HFO-1234yf was synthesized by dehydrofluorination of HFC-245cb; and HFO-1225ye was synthesized by dehydrofluorination of HFC-236ea.

(4) The application of the chromium-free gas phase fluorination catalyst according to the present invention.

When HCFO-1233xf is synthesized by gas phase fluorination of HCC-1230xa, after a reaction time of 20 hours, the conversion rate of HCC-1230xa is up to 100% and the selectivity to HCFO-1233xf is up to 99.6%; and after a reaction time of 1,000 hours, the conversion rate of HCC-1230xa is up to 100%, and the selectivity to HCFO-1233xf is up to 93.4%.

When HCFO-1233xf is synthesized by gas phase fluorination of HCC-240ab, after a reaction time of 20 hours, the conversion rate of HCC-240ab is 100% and the selectivity to HCFO-1233xf is up to 98.8%; and after a reaction time of 1,000 hours, the conversion rate of HCC-240ab is 100%, and the selectivity to HCFO-1233xf was 91.9%.

When HCFO-1233xf is synthesized by gas phase fluorination of HCC-240db, after a reaction time of 20 hours, the conversion rate of HCC-240db is up to 100% and the selectivity to HCFO-1233xf is up to 98.4%; and after a reaction time of 1,000 hours, the conversion rate of HCC-240db is up to 100%, and the selectivity to HCFO-1233xf is up to 91.6%.

When HCFO-1233xf is synthesized by gas phase fluorination of HCC-1230xf, after a reaction time of 20 hours, the conversion rate of HCC-1230xf is up to 100% and the selectivity to HCFO-1233xf is up to 99.5%; and after a reaction time of 1,000 hours, the conversion rate of HCC-1230xf is up to 100%, and the selectivity to HCFO-1233xf is up to 93.7%.

When HCFO-1233zd is synthesized by gas phase fluorination of HCC-240fa, after a reaction time of 20 hours, the conversion rate of HCC-240fa is up to 100% and the selectivity to HCFO-1233zd is up to 99.2%; and after a reaction time of 1,000 hours, the conversion rate of HCC-240fa is up to 100%, and the selectivity to HCFO-1233zd is up to 93.5%.

When HFO-1243zf is synthesized by gas phase fluorination of TCP, after a reaction time of 20 hours, the conversion rate of tetrachloropropane is up to 100% and the selectivity to HFO-1243zf is up to 97.6%; and after a reaction time of 1,000 hours, the conversion rate of tetrachloropropane is up to 100%, and the selectivity to HFO-1243zf is up to 90.5%.

In conclusion, the chromium-free gas phase fluorination catalyst according to the present invention has the advantages such as environmentally friendly of chromium-free, long service life of the catalyst and good catalytic activity.

BEST MODE FOR CARRYING OUT THE PRESENT INVENTION

The compound containing iron element according to the present invention is iron oxide, iron hydroxide, ferric chloride, ferric sulfate, ferric nitrate, ferric oxalate, ferric ammonium thiocyanate, Thenard's Blue, ferric diamminochloride and the like, preferably iron salt compound, iron oxide or iron hydroxide.

The rare earth metal element according to the present invention is one selected from Sc, Y, Ce, La, Nd, Pr, Pm, Sm, Eu, Gd, Tb, Yb, Ho, Dy, Er, Tm and Lu, preferably Y, Ce, La, Pr and Tb. Specific compounds are rare earth oxides such as samarium oxide, neodymium oxide, lanthanum oxide, terbium oxide, cerium oxide and thulium oxide; rare earth hydroxides such as cerium hydroxide, lanthanum hydroxide, yttrium hydroxide, praseodymium hydroxide, neodymium hydroxide, samarium hydroxide, europium hydroxide, gadolinium hydroxide, terbium hydroxide, dysprosium hydroxide, holmium hydroxide, thulium hydroxide, ytterbium hydroxide and lutetium hydroxide; rare earth nitrates such as cerium nitrate, lanthanum nitrate, yttrium nitrate, praseodymium nitrate, gadolinium nitrate, neodymium nitrate, europium nitrate, dysprosium nitrate, scandium nitrate, erbium nitrate, terbium nitrate, ytterbium nitrate, holmium nitrate, thorium nitrate and lutetium nitrate; rare earth chloride salts such as cerium chloride, lanthanum chloride, praseodymium chloride, neodymium chloride, yttrium chloride, samarium chloride, europium chloride, gadolinium chloride, dysprosium chloride, ytterbium chloride, holmium chloride, erbium chloride and terbium chloride; rare earth acetates such as cerium acetate, lanthanum acetate, europium acetate, dysprosium acetate, yttrium acetate, samarium acetate, gadolinium acetate, praseodymium acetate, neodymium acetate, holmium acetate, terbium acetate and erbium acetate; or rare earth double salts such as ammonium cerium nitrate and ammonium cerium sulfate.

The compound containing element A in the precursor of the chromium-free gas phase fluorination catalyst according to the present invention is a catalyst support, wherein the element A is one selected from Ca, Al, Mg and Ti. For example, the compound containing element A is calcium carbonate, magnesium carbonate, calcium chloride, magnesium chloride, aluminum chloride, calcium oxide, alumina oxide, magnesium oxide, titanium dioxide, calcium hydroxide, magnesium hydroxide, aluminum hydroxide, calcium acetate, magnesium acetate, aluminum acetate, calcium hypochlorite or magnesium perchlorate, and the like, preferably corresponding metallic salt compound, metal oxide or metal hydroxide of the element A.

The preparation method of the chromium-free gas phase fluorination catalyst according to the present invention is not limited, and any known preparation method for gas phase fluorination catalysts may be suitable for the present invention. Preferably, the present invention utilizes an impregnation method, a co-precipitation method and a blending method to prepare various chromium-free gas phase fluorination catalysts according to the present invention. During roasting, the catalyst will be subjected to physical and chemical changes such as thermal decomposition, solid-phase reaction, changes in crystal form, recrystallization and sintering, which play an important role in the preparation of the catalyst. The roasting atmosphere of the chromium-free gas phase fluorination catalyst according to the present invention is not limited, and the roasting may be conducted in different roasting atmospheres such as air, hydrogen and nitrogen. Fluorination is an important step which affects the activity of the catalyst. After high-temperature roasting, the precursor of the chromium-free gas phase fluorination catalyst according to the present invention is fluorinated with hydrogen fluoride preferably at a temperature of 400° C. More preferably, the initial fluorination temperature is 300° C. and then gradually heated to 400° C. to continue the fluorination reaction for 8 hours.

The type of the reactor used for the fluorination reaction is not critical. Any suitable reactor for gas phase fluorination may be applied to the present invention. Preferably, it is preferable in the present invention to use a tube fixed-bed reactor made from a material resistant to hydrogen fluoride corrosion such as nickel and alloys thereof (including Hastelloy, Inconel, Incoloy and Monel).

The chromium-free gas phase fluorination catalyst according to the present invention is suitable for preparation of HFOs or HCFOs by gas phase fluorination of halohydrocarbons. The halohydrocarbons may be 1,1,1,3-tetrachloropropane (TCP), 1,1,1,3,3-pentachloropropane (HCC-240fa), 1,1,1,2,2-pentachloropropane (HCC-240ab), 1,1,1,2,3-pentachloropropane (HCC-240db), 1-chloro-3,3,3-trifluoropropene (HCFO-1233zd), 3-chloro-1,1,1,3-tetrafluoropropane (HCFC-244fa), 1,1,2,3-tetrachloropropene (HCC-123 Oxa), 2,3,3,3-tetrachloropropene (HCC-1230xf), 2-chloro-3,3,3-trifluoropropene (HCFO-1233xf), 2-chloro-1,1,1,2-tetrafluoropropane (HCFC-244bb), 1,1,1,2,3-pentafluoropropane (HFC-245eb), 1,1,1,2,2-pentafluoropropane (HFC-245cb), 1,1,1,3,3-pentafluoropropane (HFC-245fa), 1,1,1,2,3,3-hexafluoropropane (HFC-236ea) and the like. HFOs or HCFOs may be trifluoropropene (HFO-1243zf), HCFO-1233zd, 1,3,3,3-tetrafluoropropene (HFO-1234ze), HCFO-1233xf, 2,3,3,3-tetrafluoropropene (HFO-1234yf), 1,1,1,2,3-pentafluoropropene (HFO-1225ye) and the like.

The technical solutions of the present invention will be further explained with reference to the examples below provided by the inventors.

EXAMPLE 1

A catalyst precursor with a Fe content of 20.0%, a Mg content of 77.0% and a La content of 3.0% was prepared by dissolving a certainamount of $FeCl_3.6H_2O$, $MgCl_2.6H_2O$ and $La(NO_3)_3.6H_2O$ in water, adding precipitant ammonia water at 60° C. to the obtained solution, maintaining the PH of the solution between 7.5 and 8.5 to precipitate it completely under stirring, filtering the resulted slurry, washing the precipitate to a neutral PH with deionized water and drying the precipitate at 120° C. The precursor was then compressed and shaped. After roasting at 450° C. in a muffle furnace for 8 hours, the shaped precursor was loaded into a tubular reactor and heated to 300° C., and fluorinated for 1 hour by introducing hydrogen fluoride gas. The temperature was increased to 400° C. at a heating rate of 1° C./min, and the fluorination reaction was continued for 8 hours to obtain a chromium-free gas phase fluorination catalyst.

60 ml chromium-free gas phase fluorination catalyst obtained in Example 1 was loaded into a nickel tubular fixed-bed reactor with an inner diameter of 38 mm. HF and 1,1,2,3-tetrachloropropene (HCC-1230xa) were introduced into the reactor to conduct the reaction. The molar ratio of HF to HCC-1230xa was controlled to be 15:1; the contact time was 10.9 seconds; and the reaction temperature was 260° C. After a reaction time of 20 hours, the reaction products were subjected to water washing and alkaline washing to remove HCl and HF, and then analyzed by gas chromatography. The conversion rate of HCC-1230xa was 100% and the selectivity to HCFO-1233xf was 99.4%. After a reaction time of 1,000 hours, the reaction products were subjected to water washing and alkaline washing to remove HCl and HF, and then analyzed by gas chromatography. The conversion rate of HCC-1230xa was 100% and the selectivity to HCFO-1233xf was 92.5%.

EXAMPLE 2

The catalyst preparation process in Example 2 was substantially the same as that in Example 1 except that $MgCl_2.6H_2O$ was replaced with $CaCl_2$ and $La(NO_3)_3.6H_2O$ was replaced with $Y(NO_3)_3.6H_2O$. The obtained catalyst precursor had a Fe content of 20.0%, a Ca content of 77.0% and a Y content of 3.0%. The precursor was then compressed and shaped. After roasting at 450° C. in a muffle furnace for 8 hours, the shaped precursor was loaded into a tubular reactor and heated to 300° C., and fluorinated for 1 hour by introducing hydrogen fluoride gas. The temperature was increased to 400° Cat a heating rate of 1° C./min, and the fluorination reaction was continued for 8 hours to obtain a chromium-free gas phase fluorination catalyst.

50 ml chromium-free gas phase fluorination catalyst obtained in Example 2 was loaded into a nickel tubular fixed-bed reactor with an inner diameter of 38 mm. HF and 1,1,1,3,3-pentachloropropane (HCC-240fa) were introduced into the reactor to conduct the reaction. The molar ratio of HF to HCC-240fa was 15:1; the contact time was 10.9 seconds; and the reaction temperature was 240° C. After a reaction time of 20 hours, the reaction products were subjected to water washing and alkaline washing to remove HCl and HF, and then analyzed by gas chromatography. The conversion rate of HCC-240fa was 100% and the selectivity for HCFO-1233zd was 99.2%. After a reaction time of 1,000 hours, the reaction products were subjected to water washing and alkaline washing to remove HCl and HF, and then analyzed by gas chromatography. The conversion rate of HCC-240fa was 100% and the selectivity for HCFO-1233zd was 93.5%.

EXAMPLE 3

The catalyst preparation process in Example 3 was substantially the same as that in Example 1 except that $MgCl_2.6H_2O$ was replaced with $AlCl_3.6H_2O$ and $La(NO_3)_3.6H_2O$ was replaced with $Ce(NO_3)_3.6H_2O$. The obtained catalyst precursor had a Fe content of 20.0%, a Al content of 77.0% and a Ce content of 3.0%. The precursor was then compressed and shaped. After roasting at 450° C.

in a muffle furnace for 8 hours, the shaped precursor was loaded into a tubular reactor and heated to 300° C., and fluorinated for 1 hour by introducing hydrogen fluoride gas. The temperature was increased to 400° C at a heating rate of 1° C./min, and the fluorination reaction was continued for 8 hours to obtain a chromium-free gas phase fluorination catalyst.

30 ml chromium-free gas phase fluorination catalyst obtained in Example 3 was loaded into a nickel tubular fixed-bed reactor with an inner diameter of 38 mm. HF and tetrachloropropane were introduced into the reactor to conduct the reaction. The molar ratio of HF to tetrachloropropane was 15:1; the contact time was 3.2 seconds; and the reaction temperature was 260° C. After a reaction time of 20 hours, the reaction products were subjected to water washing and alkaline washing to remove HCl and HF, and then analyzed by gas chromatography. The conversion rate of tetrachloropropane was 100% and the selectivity for HFO-1243zf was 97.6%. After a reaction time of 1,000 hours, the reaction products were subjected to water washing and alkaline washing to remove HCl and HF, and then analyzed by gas chromatography. The conversion rate of tetrachloropropane was 100% and the selectivity for HFO-1243zf was 90.5%.

EXAMPLE 4

The catalyst preparation process in Example 4 was substantially the same as that in Example 1 except that La(NO$_3$)$_3$.6H$_2$O was replaced with Sc(NO$_3$)$_3$.6H$_2$O. The obtained catalyst precursor had a Fe content of 20.0%, a Mg content of 77.0% and a Sc content of 3.0%. The precursor was then compressed and shaped. After roasting at 450° C. in a muffle furnace for 8 hours, the shaped precursor was loaded into a tubular reactor and heated to 300° C., and fluorinated for 1 hour by introducing hydrogen fluoride gas. The temperature was increased to 400° C at a heating rate of 1° C./min, and the fluorination reaction was continued for 8 hours to obtain a chromium-free gas phase fluorination catalyst.

60 ml chromium-free gas phase fluorination catalyst obtained in Example 4 was loaded into a nickel tubular fixed-bed reactor with an inner diameter of 38 mm. HF and 1,1,1,2,2-pentachloropropane (HCC-240ab) were introduced into the reactor to conduct the reaction. The molar ratio of HF to HCC-240ab was 15:1; the contact time was 10.9 seconds; and the reaction temperature was 260° C. After a reaction time of 20 hours, the reaction products were subjected to water washing and alkaline washing to remove HCl and HF, and then analyzed by gas chromatography. The conversion rate of HCC-240ab was 100% and the selectivity for HCFO-1233xf was 98.8%. After a reaction time of 1,000 hours, the reaction products were subjected to water washing and alkaline washing to remove HCl and HF, and then analyzed by gas chromatography. The conversion rate of HCC-240ab was 100% and the selectivity for HCFO-1233xf was 91.9%.

EXAMPLE 5

The catalyst preparation process in Example 5 was substantially the same as that in Example 1 except that La(NO$_3$)$_3$.6H$_2$O was replaced with Nd(NO$_3$)$_3$.6H$_2$O. The obtained catalyst precursor had a Fe content of 20.0%, a Mg content of 77.0% and a Nd content of 3.0%. The precursor was then compressed and shaped. After roasting at 450° C. in a muffle furnace for 8 hours, the shaped precursor was loaded into a tubular reactor and heated to 300° C., and fluorinated for 1 hour by introducing hydrogen fluoride gas. The temperature was increased to 400° C at a heating rate of 1° C./min, and the fluorination reaction was continued for 8 hours to obtain a chromium-free gas phase fluorination catalyst.

60 ml chromium-free gas phase fluorination catalyst obtained in Example 5 was loaded into a nickel tubular fixed-bed reactor with an inner diameter of 38 mm. HF and 1,1,1,2,3-pentachloropropane (HCC-240db) were introduced to conduct the reaction. The molar ratio of HF to HCC-240db was 10:1; the contact time was 10.9 seconds; and the reaction temperature was 260° C. After a reaction time of 20 hours, the reaction products were subjected to water washing and alkaline washing to remove HCl and HF, and then analyzed by gas chromatography. The conversion rate of HCC-240db was 100% and the selectivity for HCFO-1233xf was 98.4%. After a reaction time of 1,000 hours, the reaction products were subjected to water washing and alkaline washing to remove HCl and HF, and then analyzed by gas chromatography. The conversion rate of HCC-240db was 100% and the selectivity for HCFO-1233xf was 91.6%.

EXAMPLE 6

The catalyst preparation process of Example 6 was substantially the same as that of Example 1 except that La(NO$_3$)$_3$.6H$_2$O was replaced with Pr(NO$_3$)$_3$.6H$_2$O. The obtained catalyst precursor had a Fe content of 20.0%, a Mg content of 77.0% and a Pr content of 3.0%. The precursor was then compressed and shaped. After roasting at 450° C. in a muffle furnace for 8 hours, the shaped precursor was loaded into a tubular reactor and heated to 300° C., and fluorinated for 1 hour by introducing hydrogen fluoride gas. The temperature was increased to 400° C. at a heating rate of 1° C./min, and the fluorination reaction was continued for 8 hours to obtain a chromium-free gas phase fluorination catalyst.

60 ml chromium-free gas phase fluorination catalyst obtained in Example 6 was loaded into a nickel tubular fixed-bed reactor with an inner diameter of 38 mm. HF and 2,3,3,3-tetrachloropropene (HCC-1230xf) were introduced into the reactor to conduct the reaction. The molar ratio of HF to HCC-1230xf was 10:1; the contact time was 10.9 seconds; and the reaction temperature was 260° C. After a reaction time of 20 hours, the reaction products were subjected to water washing and alkaline washing to remove HCl and HF, and then analyzed by gas chromatography. The conversion rate of HCC-1230xf was 100% and the selectivity for HCFO-1233xf was 99.5%. After a reaction time of 1,000 hours, the reaction products were subjected to water washing and alkaline washing to remove HCl and HF, and then analyzed by gas chromatography. The conversion rate of HCC-1230xf was 100% and the selectivity for HCFO-1233xf was 93.7%.

EXAMPLE 7

The catalyst preparation process in Example 7 was substantially the same as that in Example 1 except that La(NO$_3$)$_3$.6H$_2$O was replaced with Tb(NO$_3$)$_3$.6H$_2$O. The obtained catalyst precursor had a Fe content of 15.0%, a Ca content of 83.5% and a Tb content of 1.5%. The precursor was then compressed and shaped. After roasting at 450° C. in a muffle furnace for 8 hours, the shaped precursor was loaded into a tubular reactor and heated to 300° C., and fluorinated for 1 hour by introducing hydrogen fluoride gas.

The temperature was increased to 400° C. at a heating rate of 1° C./min, and the fluorination reaction was continued for 8 hours to obtain a chromium-free gas phase fluorination catalyst.

60 ml chromium-free gas phase fluorination catalyst obtained in Example 7 was loaded into a nickel tubular fixed-bed reactor with an inner diameter of 38 mm. HF and 1,1,2,3-tetrachloropropene (HCC-1230xa) were introduced into the reactor conduct the reaction. The molar ratio of HF to HCC-1230xf was 15:1; the contact time was 10.9 seconds; and the reaction temperature was 260° C. After a reaction time of 20 hours, the reaction products were subjected to water washing and alkaline washing to remove HCl and HF, and then analyzed by gas chromatography. The conversion rate of HCC-1230xa was 100% and the selectivity for HCFO-1233xf was 99.6%. After a reaction time of 1,000 hours, the reaction products were subjected to water washing and alkaline washing to remove HCl and HF, and then analyzed by gas chromatography. The conversion rate of HCC-1230xa was 100% and the selectivity for HCFO-1233xf was 93.4%.

EXAMPLE 8

α-$Fe_2O_3$, MgO and $Yb_2O_3$ were mixed well with a Fe content of 5.0%, a Mg content of 94.5% and a Tb content of 0.5%. The mixture was compressed and shaped to obtain a catalyst precursor. After roasting at 450° C. in a muffle furnace for 8 hours, the obtained catalyst precursor was loaded into a tubular reactor and heated to 300° C., and fluorinated with hydrogen fluoride gas for 1 hour. The temperature was increased to 400° C. at a heating rate of 1° C./min, and the fluorination reaction was continued for 8 hours to obtain a chromium-free gas phase fluorination catalyst.

60 ml chromium-free gas phase fluorination catalyst obtained in Example 8 was loaded into a nickel tubular fixed-bed reactor with an inner diameter of 38 mm. HF and HCFC-1233zd were introduced into the reactor to conduct the reaction. The molar ratio of HF to HCFC-1233zd was 10:1; the contact time was 2 seconds; and the reaction temperature was 380° C. After a reaction time of 20 hours, the reaction products were subjected to water washing and alkaline washing to remove HCl and HF, and then analyzed by gas chromatography. The conversion rate of HCFC-1233zd was 86% and the selectivity for the effective component HFO-1234ze was 97.0%. After a reaction time of 300 hours, the reaction products were subjected to water washing and alkaline washing to remove HCl and HF, and then analyzed by gas chromatography. The conversion rate of HCFC-1233zd was 70% and the selectivity for the effective component HFO-1234ze was 92.4%.

EXAMPLE 9

γ-FeO(OH), $MgCO_3$, $Ho_2O_3$ and $Dy_2O_3$ were mixed well with a Fe content of 50.0%, a Mg content of 45.0%, a Ho content of 2.0% and a Dy content of 3.0%. The mixture was compressed and shaped to obtain a catalyst precursor. After roasting at 450° C. in a muffle furnace for 8 hours, the obtained catalyst precursor was loaded into a tubular reactor and heated to 300° C., and fluorinated with hydrogen fluoride gas for 1 hour. The temperature was increased to 400° Cat a heating rate of 1° C./min, and the fluorination reaction was continued for 8 hours to obtain a chromium-free gas phase fluorination catalyst.

60 ml chromium-free gas phase fluorination catalyst obtained in Example 9 was loaded into a nickel tubular fixed-bed reactor with an inner diameter of 38 mm. HF and HCFO-1233xf were introduced into the reactor to conduct the reaction. The contact time was 10 seconds; and the reaction temperature was 330° C. After a reaction time of 20 hours, the reaction products were subjected to water washing and alkaline washing to remove HCl and HF, and then analyzed by gas chromatography. The conversion rate of HCFO-1233xf was 65.2% and the selectivity for the effective component HCFC-244bb was 97.0%. After a reaction time of 300 hours, the reaction products were subjected to water washing and alkaline washing to remove HCl and HF, and then analyzed by gas chromatography. The conversion rate of HCFO-1233xf was 50.0% and the selectivity for the effective component HCFC-244bb was 94.5%.

EXAMPLE 10

β-FeO(OH), $CaCO_3$, $Eu(OH)_3$ and $Gd(OH)_3$ were mixed well with a Fe content of 50.0%, a Ca content of 45.0%, a Eu content of 2.5% and a Gd content of 2.5%. The mixture was compressed and shaped to obtain a catalyst precursor. After roasting at 450° C. in a muffle furnace for 8 hours, the obtained catalyst precursor was loaded into a tubular reactor and heated to 300° C., and fluorinated with hydrogen fluoride gas for 1 hour. The temperature was increased to 400° C. at a heating rate of 1° C./min, and the fluorination reaction was continued for 8 hours to obtain a chromium-free gas phase fluorination catalyst.

60 ml fluorination catalyst obtained in Example 10 was loaded into a nickel tubular fixed-bed reactor with an inner diameter of 38 mm. HFC-236ea was introduced into the reactor to conduct the reaction. The contact time was 30 seconds; and the reaction temperature was 400° C. After a reaction time of 20 hours, the reaction products were subjected to water washing and alkaline washing to remove HF, and then analyzed by gas chromatography. The conversion rate of HFC-236ea was 66.4% and the selectivity for HFO-1225ye was 98.0%. After a reaction time of 500 hours, the reaction products were subjected to water washing and alkaline washing to remove HF, and then analyzed by gas chromatography. The conversion rate of HFC-236ea was 52.0% and the selectivity for HFO-1225ye was 92.4%.

EXAMPLE 11

γ-$Fe_2O_3$, CaO, $Pm_2(C_2O_4)_3$ and $Sm_2(C_2O_4)_3$ were mixed well with a Fe content of 50.0%, a Ca content of 45.0%, a Pm content of 2.5% and a Sm content of 2.5%. The mixture was compressed and shaped to obtain a catalyst precursor. After roasting at 450° C. in a muffle furnace for 8 hours, the obtained catalyst precursor was loaded into a tubular reactor and heated to 300° C., and fluorinated with hydrogen fluoride gas for 1 hour. The temperature was increased to 400° C. at a heating rate of 1° C./min, and the fluorination reaction was continued for 8 hours to obtain a chromium-free gas phase fluorination catalyst.

60 ml chromium-free gas phase fluorination catalyst obtained in Example 11 was loaded into a nickel tubular fixed-bed reactor with an inner diameter of 38 mm. HFC-245fa were introduced into the reactor to conduct the reaction. The contact time was 30 seconds; and the reaction temperature was 380° C. After a reaction time of 20 hours, the reaction products were subjected to water washing and alkaline washing to remove HF, and then analyzed by gas chromatography. The conversion rate of HFC-245fa was 86.4% and the selectivity for E-HFO-1234ze was 94.0%. After a reaction time of 300 hours, the reaction products were subjected to water washing and alkaline washing to remove HF, and then analyzed by gas chromatography. The conversion rate of HFC-245fa was 75.0% and the selectivity for E-HFO-1234ze was 90.0%.

EXAMPLE 12

β-FeO(OH), Al(OH)$_3$ and Er$_2$O$_3$ were mixed well with a Fe content of 50.0%, a Al content of 45.0% and a Er content of 5.0%. The mixture was compressed and shaped to obtain a catalyst precursor. After roasting at 450° C. in a muffle furnace for 8 hours, the obtained catalyst precursor was loaded into a tubular reactor and heated to 300° C., and fluorinated with hydrogen fluoride gas for 1 hour. The temperature was increased to 400° C. at a heating rate of 1° C./min, and the fluorination reaction was continued for 8 hours to obtain a chromium-free gas phase fluorination catalyst.

60 ml chromium-free gas phase fluorination catalyst obtained in Example 12 was loaded into a nickel tubular fixed-bed reactor with an inner diameter of 38 mm. HFC-245eb were introduced into the reactor to conduct the reaction. The contact time was 30 seconds; and the reaction temperature was 400° C. After a reaction time of 20 hours, the reaction products were subjected to water washing and alkaline washing to remove HF, and then analyzed by gas chromatography. The conversion rate of HFC-245eb was 92.4% and the selectivity for HFO-1234yf was 98.0%. After a reaction time of 500 hours, the reaction products were subjected to water washing and alkaline washing to remove HF, and then analyzed by gas chromatography. The conversion rate of HFC-245eb was 75.5% and the selectivity for HFO-1234yf was 92.4%.

EXAMPLE 13

δ-FeO(OH), CaO and Tm(OH)$_3$ were mixed well with a Fe content of 50.0%, a Ca content of 45.0% and a Tm content of 5.0%. The mixture was compressed and shaped to obtain a catalyst precursor. After roasting at 450° C. in a muffle furnace for 8 hours, the obtained catalyst precursor was loaded into a tubular reactor and heated to 300° C., and fluorinated with hydrogen fluoride gas for 1 hour. The temperature was increased to 400° C. at a heating rate of 1° C./min, and the fluorination reaction was continued for 8 hours to obtain a chromium-free gas phase fluorination catalyst.

60 ml chromium-free gas phase fluorination catalyst obtained in Example 13 was loaded into a nickel tubular fixed-bed reactor with an inner diameter of 38 mm. HFC-245cb was introduced into the reactor to conduct the reaction. The contact time was 30 seconds; and the reaction temperature was 360° C. After a reaction time of 20 hours, the reaction products were subjected to water washing and alkaline washing to remove HF, and then analyzed by gas chromatography. The conversion rate of HFC-245cb was 96.4% and the selectivity for HFO-1234yf was 98.4%. After a reaction time of 500 hours, the reaction products were subjected to water washing and alkaline washing to remove HF, and then analyzed by gas chromatography. The conversion rate of HFC-245cb was 80.2% and the selectivity for HFO-1234yf was 94.4%.

EXAMPLE 14

An impregnation solution was prepared by dissolving a certain amount of FeCl$_3$.6H$_2$O and a certain amount of Lu(NO$_3$)$_3$.6H$_2$O in 100 ml distilled water. The TiO$_2$ support was then placed and impregnated in the impregnation solution for 5 hours, and dried through evaporation on a rotary evaporator at 60° C. to obtain the precursor of the chromium-free gas phase fluorination catalyst with a Fe content of 20.0%, a Ti content of 75.0% and a Lu content of 5.0%. After roasting at 450° C. in a muffle furnace for 8 hours, the obtained catalyst precursor was loaded into a tubular reactor and heated to 300° C., and fluorinated with hydrogen fluoride gas for 1 hour. The temperature was increased to 400° C. at a heating rate of 1° C./min, and the fluorination reaction was continued for 8 hours to obtain a chromium-free gas phase fluorination catalyst.

60 ml chromium-free gas phase fluorination catalyst obtained in Example 14 was loaded into a nickel tubular fixed-bed reactor with an inner diameter of 38 mm. HCFC-244fa was introduced into the reactor to conduct the reaction. The contact time was 20 seconds; and the reaction temperature was 380° C. After a reaction time of 20 hours, the reaction products were subjected to water washing and alkaline washing to remove HCl, and then analyzed by gas chromatography. The conversion rate of HCFC-244fa was 95.0% and the selectivity for HFO-1234ze was 95.0%. After a reaction time of 500 hours, the reaction products were subjected to water washing and alkaline washing to remove HCl, and then analyzed by gas chromatography. The conversion rate of HCFC-244fa was 80.2% and the selectivity for HFO-1234ze was 92.4%.

EXAMPLE 15

An impregnation solution was prepared by dissolving a certain amount of FeCl$_3$.6H$_2$O and a certain amount of Ce(NO$_3$)$_3$.6H$_2$O in 100 ml distilled water. The TiO$_2$ support was then placed and impregnated in the impregnation solution for 5 hours, and dried through evaporation on a rotary evaporator at 60° C. to obtain the precursor of the chromium-free gas phase fluorination catalyst with a Fe content of 20.0%, a Ti content of 75.0% and a Ce content of 5.0%. After roasting at 450° C. in a muffle furnace for 8 hours, the obtained catalyst precursor was loaded into a tubular reactor and heated to 300° C., and fluorinated with hydrogen fluoride gas for 1 hour. The temperature was increased to 400° C. at a heating rate of 1° C./min, and the fluorination reaction was continued for 8 hours to obtain a chromium-free gas phase fluorination catalyst.

60 ml chromium-free gas phase fluorination catalyst obtained in Example 15 was loaded into a nickel tubular fixed-bed reactor with an inner diameter of 38 mm. HCFC-244bb was introduced into the reactor to conduct the reaction. The contact time was 20 seconds; and the reaction temperature was 380° C. After a reaction time of 20 hours, the reaction products were subjected to water washing and alkaline washing to remove HCl, and then analyzed by gas chromatography. The conversion rate of HCFC-244bb was 68.0% and the selectivity to HFO-1234yf was 99.0%. After a reaction time of 500 hours, the reaction products were subjected to water washing and alkaline washing to remove HCl, and then analyzed by gas chromatography. The conversion rate of HCFC-244bb was 36.2% and the selectivity for HFO-1234yf was 96.7%.

What is claimed is:
1. A chromium-free gas phase fluorination catalyst, wherein a precursor of the catalyst consists of a compound containing iron, a compound containing a rare earth metal element and a compound containing element A, wherein the element A is selected from the group consisting of Ca, Al,

Mg and Ti, and wherein the precursor has been subjected to roasting and fluorination to obtain the chromium-free gas phase fluorination catalyst.

2. The chromium-free gas phase fluorination catalyst according to claim 1, wherein the precursor of the catalyst comprises the iron, the rare earth metal element and the element A in following mass percent compositions: 5.0%-50.0% of the iron, 0.5%-5.0% of the rare earth metal element, and 45.0-94.5% of the element A; and the sum of the mass percent of the iron, rare earth metal element and element A is 100%.

3. The chromium-free gas phase fluorination catalyst according to claim 1, wherein the precursor of the catalyst has been roasted at 400-500° C. and fluorinated with hydrogen fluoride gas at 350-450° C. to obtain the chromium-free gas phase fluorination catalyst.

4. The chromium-free gas phase fluorination catalyst according to claim 1, wherein:
the compound containing iron is an oxyhalide of iron, a metallic salt compound of iron, an oxide of iron, a hydroxide of iron, an organic salt containing the iron or a complex containing the iron;
the compound containing the rare earth metal element is a metallic salt compound of the rare earth metal element, an oxide of the rare earth metal element, a hydroxide of the rare earth metal element, an organic salt containing the rare earth metal element or a rare earth double salt containing the rare earth metal element; and
the compound containing element A is an oxyhalide of the element A, a metallic salt compound of the element A, an oxide of the element A, a hydroxide of the element A, an organic salt containing the element A or a complex containing the element A.

5. The chromium-free gas phase fluorination catalyst according to claim 1, wherein the iron is ferric iron with a crystal form of $\alpha$, $\beta$, $\gamma$, or $\delta$.

6. The chromium-free gas phase fluorination catalyst according to claim 1, wherein the compound containing the rare earth metal element is a single compound containing the rare earth metal element or a composition of two or more compounds containing the rare earth metal element, wherein the rare earth metal element is selected from the group consisting of Sc, Y, Ce, La, Nd, Pr, Pm, Sm, Eu, Gd, Tb, Yb, Ho, Dy, Er, Tm and Lu.

* * * * *